(12) United States Patent
Prasad et al.

(10) Patent No.: US 11,352,556 B2
(45) Date of Patent: Jun. 7, 2022

(54) PROCESS FOR THE SYNTHESIS OF AIR STABLE METAL SULPHIDE QUANTUM DOTS

(71) Applicant: COUNCIL OF SCIENTIFIC & INDUSTRIAL RESEARCH, New Delhi (IN)

(72) Inventors: Bhagavatula Lakshmi Vara Prasad, Pune (IN); Abhjit Bera, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 575 days.

(21) Appl. No.: 16/344,580

(22) PCT Filed: Oct. 27, 2017

(86) PCT No.: PCT/IN2017/050498
§ 371 (c)(1),
(2) Date: Apr. 24, 2019

(87) PCT Pub. No.: WO2018/078654
PCT Pub. Date: May 3, 2018

(65) Prior Publication Data
US 2020/0048543 A1 Feb. 13, 2020

(30) Foreign Application Priority Data
Oct. 28, 2016 (IN) .............................. 201611037019

(51) Int. Cl.
| | |
|---|---|
| *C09K 11/02* | (2006.01) |
| *C09K 11/56* | (2006.01) |
| *C09K 11/66* | (2006.01) |
| *C07C 329/12* | (2006.01) |
| *C01G 11/02* | (2006.01) |
| *C01G 9/08* | (2006.01) |
| *B01J 13/00* | (2006.01) |
| *C01G 21/21* | (2006.01) |
| *C01G 45/00* | (2006.01) |
| *C09K 11/57* | (2006.01) |
| *B82Y 20/00* | (2011.01) |
| *B82Y 40/00* | (2011.01) |
| *H01L 31/0232* | (2014.01) |
| *H01L 31/055* | (2014.01) |
| *H01L 33/50* | (2010.01) |

(52) U.S. Cl.
CPC ......... *C09K 11/025* (2013.01); *B01J 13/0026* (2013.01); *C01G 9/08* (2013.01); *C01G 11/02* (2013.01); *C01G 21/21* (2013.01); *C01G 45/00* (2013.01); *C07C 329/12* (2013.01); *C09K 11/565* (2013.01); *C09K 11/572* (2013.01); *C09K 11/661* (2013.01); *B82Y 20/00* (2013.01); *B82Y 40/00* (2013.01); *C01P 2002/72* (2013.01); *C01P 2002/84* (2013.01); *C01P 2004/04* (2013.01); *C01P 2004/64* (2013.01); *C01P 2006/60* (2013.01); *H01L 31/02322* (2013.01); *H01L 31/055* (2013.01); *H01L 33/502* (2013.01)

(58) Field of Classification Search
CPC ... C09K 11/025; C09K 11/565; C09K 11/572; C09K 11/661; C01G 11/02; C01G 21/21; C01G 45/00; C01G 9/08; C01P 2002/72; C01P 2002/84; C01P 2004/04; C01P 2004/64; C01P 2006/60; H01L 31/02322; H01L 31/055; H01L 31/502; C07D 487/04; C07C 329/12; B01J 13/0026; B82Y 40/00
See application file for complete search history.

(56) References Cited

U.S. PATENT DOCUMENTS

| | | | |
|---|---|---|---|
| 2006/0078490 A1 | 4/2006 | Shih et al. | |
| 2009/0084307 A1* | 4/2009 | Cao | C30B 7/00 117/11 |
| 2018/0148638 A1* | 5/2018 | Ahn | C09K 11/06 |

OTHER PUBLICATIONS

Lin et al., A facile route to (ZnS)x(CuInS2)1-x hierarchical microspheres with excellent water-splitting ability, 2012, Journal of Materials Chemistry, 22, pp. 22619-22623. (Year: 2012).*
Yaping Du et al., "Near-Infrared Photo luminescent Ag2S Quantum Dots from a single source precursor," Journal of American Chemical Society, 2010, 132 (5), pp. 1470-1471.
Samad Mussa Farkhani et al., "Review: three synthesis methods of CdX (X=Se,S or Te) quantum dots," IET Nanobiotechnotogy, 2014, vol. 8, Iss. 2, pp. 69-76.
B.L.V. Prasad et al., "Citrate-capped quantum dots of CdSe for the selective photometric detection of silver ions in aqueous solutions," Materials Science and Engineering: B, 2010, 168(1-3), pp. 60-65.
Masayuki Kanehara et al., "Large-scale synthesis of high-quality metal sulfide semiconductor Quantum Dots with tunable surace-plasmon resonance frequencies," Chemistry A European Journal, 2012, 18(30), pp. 9230-9238.
Zhihua Zhang et al., "From metal thiobenzoates to metal sulfide nanocrystals: An experimental and theoretical investigation," Nanomaterials, 2012, 2, 113-133.
Illan J. Kramer et al., "The architecture of colloidal Quantum Dot solar cells: materials to devices," Chemical Reviews, 2014, 114, 863-882.

(Continued)

*Primary Examiner* — Matthew E. Hoban
*Assistant Examiner* — Lynne Edmondson
(74) *Attorney, Agent, or Firm* — Abelman, Frayne & Schwab; Norman Hanson; Stefan Knirr

(57) ABSTRACT

The present invention discloses a process for the preparation of metal sulphide quantum dots by using a very low cost sulphur precursor as a sulphur source. The metal sulphide quantum dots finds application in optical devices selected from photovoltaic cells, photodetectors and light-emission devices.

9 Claims, 8 Drawing Sheets

(56) References Cited

OTHER PUBLICATIONS

Serdar Celebi et al., "Synthesis and characterization of Poly(acrylic acid) stabilized Cadmium Sulfide Quantum Dots," Journal of Physical Chemistry, 2007, 111, 12668-12675.

M.A. Hines et al., "Colloidal PbS nanocrystals with size-tunable Near-Infrared Emission: Observation of post-synthesis self-narrowing of the particle size distribution," Advanced Materials, 2003, 15(21), pp. 1844-1849.

Chase C. Reinhart et al. "Colloidally Prepared 3-Mercaptopropionic Acid Capped Lead Sulfide Quantum Dots," Chemistry of Materials, 2015, 27, 7313-7320.

"Lead Sulfide Quantum Dot Synthesis" published in Clean Energy Wiki, 2012.

J.S. Steckel et al., "1.3 µm to 1.55 µm tunable electroluminescence from PbSe Quantum Dots embedded within organic device," Advanced Materials, 2003, 15(21), pp. 1862-1866.

Zhenyu Yang et al., "Colloidal Quantum Dot Photovoltaics enhanced by Perovskite Shelling," Nano Letters, 2015, 15 (11), pp. 7539-7543.

Dong-Kyun Ko et al., "Photovoltaic performance of PbS Quantum Dots treated with metal salts," ACS Nano, Feb. 2016, 10 (3), pp. 3382-3388.

\* cited by examiner

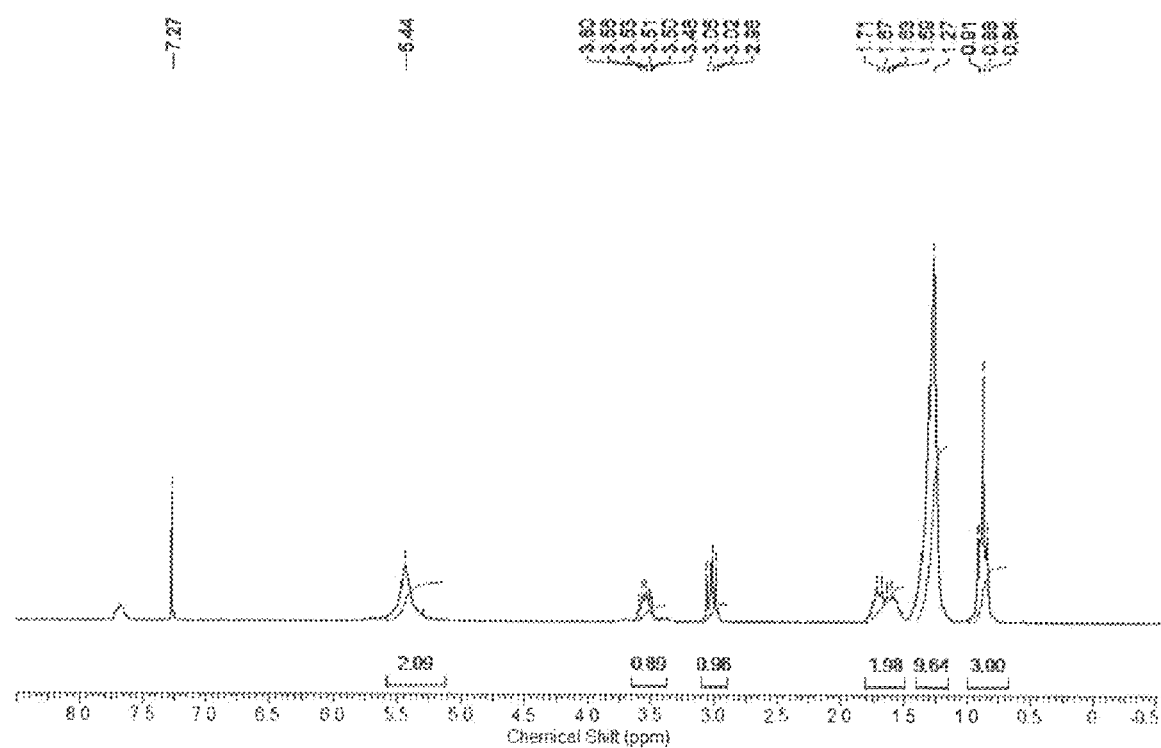
Figure: 1b

PROCESS FOR THE SYNTHESIS OF AIR STABLE METAL SULPHIDE QUANTUM DOTS

RELATED APPLICATIONS

This application is a national phase of International Application No, PCT/2017/050498 filed Oct. 27, 2017 and claims priority from Indian Patent Application No. 201611037019 file Oct. 28, 2016, both incorporated by reference in their entirety.

FIELD OF THE INVENTION

The present invention relates to a process for the preparation of metal sulphide quantum dots. More particularly, the present invention relates to a process for the preparation of metal sulphide quantum dots by using a novel and very low cost sulphur precursor as a sulphur source.

BACKGROUND AND PRIOR ART OF THE INVENTION

Colloidal quantum dots (CQDs) have received considerable attention in the past decade owing to their promise in optoelectronic devices. Colloidal quantum dots-capped with surfactant molecules and highly dispersed in solution have panned out to be extremely useful materials for the development of numerous classes of solution-processed optoelectronic devices over the past decade, including photovoltaic cells, photodetectors and light-emission devices. In addition to solution processing, a key advantage of quantum dots is the tunability in their sizes, due to which their optical and electrical properties can be readily modulated. In photovoltaic devices, doped semiconductor CQD films are combined with a metal (Schottky junction cells) or with another semiconductor (CQD-CQD or CQD-titanium dioxide p-n junctions, CQD-CQD-zinc oxide p-i-n junctions), along with asymmetric electrodes, to form a complete functional device. Lead sulfide (PbS) QDs are particularly well suited for solar energy conversion, with an absorption edge tunable from the near infrared through the visible and stability in ambient atmosphere. Solar cells based on colloidal PbS QDs could thus provide an inexpensive, flexible alternative to conventional silicon and thin-film photovoltaics (PVs).

Different physical and chemical processes are currently widely used to synthesize metal sulfide quantum dots, which allow one to obtain particles with the desired characteristics. Till date hot-injection method turned out to be the most effective method in synthesizing high quality CQD with narrow size distribution. Several metal sulfide quantum dots like CdS QD, MnS QD, ZnS QD, SnS QD, $In_2S_3$ QD and $Cu_2S$ QD have been synthesized using hot injection method and elemental sulfur or sulfur containing ligands (like thiourea) as sulphur source. In these methods generally sulphur solution is prepared by dissolving the sulphur powder in oleyl amine that leads to tire generation of $S_2$-disulfide or $Sn_2$-polysulfide which have relatively low nucleation threshold with the highly reactive Pb2+ ion. So, in case of PbS QD traditional synthetic methods using elemental sulphur limits the reaction yield and causes batch-to-batch variability and wide size distribution with low quantum yield. Due to improper surface passivation of PbS QD, prepared using elemental sulphur, their true application potential could not be realized the true application potential of this material in photovoltaic solar cell.

Article titled "Near-Infrared Photo luminescent $Ag_2S$ Quantum Dots from a single source precursor" by Yaping Du et al. published in *Journal of American Chemical Society*, 2010, 132 (5), pp 1470-1471 reports monodisperse $Ag_2S$ quantum dots (QDs) were synthesized via pyrolysis of Ag(DDTC) in oleic acid, octadecylamine, and 1-octadecene. The uniform alkyl-capped $Ag_2S$ QDs with a size of 10.2 nm emit near-IR emission at 1058 nm under 785 nm excitation. A slurry containing 0.1 mmol of Ag(DDTC) hydrate, 10 mmol of oleic acid (OA), 10 mmol of octadecylamine (ODA), and 20 mmol of 1-octadecane (ODE) in a three necked flask (100 mL) was heated to 100° C. to remove water and oxygen, thus forming a homogeneous brown solution. The resulting mixture was heated to 200° C. under $N_2$ and kept at that temperature for 30 min, affording a dark colloidal solution. After this solution was air-cooled, the nanocrystals were precipitated with excess ethanol and then washed with ethanol and dried in air at 60° C. The as-prepared products could be easily dispersed in apolar organic solvents (e.g., cyclohexane).

Article titled "Review: three synthesis methods of CdX (X=Se,S or Te) quantum dots" by Samad Mussa Farkhani et al. published in *IET Nanobiotechnology*, 2014, Vol. 8, Iss. 2, pp. 59-76 reports new methods for the synthesis of the appropriate QDs. An organometallic system for synthesis QDs consists of three components: precursors, organic surfactants and solvents. QDs synthesised in organic solvents have hydrophobic surface ligands such as trioctylphosphine (TOP), trioctylphosphine oxide (TOPO), tetradecylphosphonic acid (TDPA), oleic acid or etc. In method one these ligands of QDs surface could be replaced by some water-soluble ligand such as thiol-based molecules (such as mercaptocarbonic acids), peptides and other. This is ligands exchange. QDs can also be encapsulated by a shell of material such as silica, phospholipids, amphiphilic polymers (polyacrylic acid), polyethylene glycol (PEG)) to become biocompatible and makes them more soluble in aqueous media.

Article titled "Citrate-capped quantum dots of CdSe for the selective photometric detection of silver ions in aqueous solutions" by B.L.V. Prasad et al. published in *Materials Science and Engineering*: B, 2010, 168 (1-3), pp 60-65 reports a simple strategy for the synthesis of water soluble, luminescent, citrate-capped CdSe quantum dots (Q-CdSe) and their applications to selective detection of silver ions. For the synthesis of citrate stabilized Q-CdSe, two step procedure was used. In the first step, the precursor for Se that is, sodium seleno sulfite ($Na_2SeSO_3$) solution was prepared, which consequently allowed to react with cadmium acetate in the presence of tri-sodium citrate in the second step.

US20060078490 discloses synthesis of water soluble nanocrystalline quantum dots and uses thereof. The process involves the reaction of a water-soluble salt of a metal suitable for use in QDs with a thiol-functionalized molecule and a water-soluble sulfide. Exemplary water-soluble metal salts that may be employed in the invention are metals that can form sulfides, such as $Cd(NO_3)_2$, $Cd(ClO_4)_2$, $CdCl_2$, $CdSO_4$, cadmium acetate, $Zn(NO_3)_2$, $Zn(ClO_4)_2$, $ZnSO_4$, $ZnCl_2$, zinc acetate, $Mn(NO_3)_2$, $Mn(ClO_4)_2$, $MnSO_4$, $MnCl_2$, manganese acetate, $Pb(NO_3)_2$, $Pb(ClO_4)_2$, $PbSO_4$, $PbCl_2$, and lead acetate. The metal salt is cadmium nitrate, the thiol-containing molecule is 3-mercaptopropionic acid and the sulfide is sodium sulfide.

Article titled "Large-scale synthesis of high-quality metal sulfide semiconductor Quantum Dots with tunable surface-plasmon resonance frequencies" by Masayuki Kanehara et al. published in *Chemistry A European Journal*, 2012, 18(30), pp 9230-9238 reports high-quality CdS and Cu7S4 quantum dots (QDs) were synthesized with N,N-dibutylthioureu (DBTU) as an organic sulfur source. In this method, nucleation and growth reactions were controlled simply by the heating rate of the reaction. The mild oxidation conditions gave monodisperse CdS QDs exhibiting pure band-edge emission with relatively high photoluminescence quantum yield. During the synthesis of $Cu_7S_4$ QDs, the addition of dodecanethiol to the reaction system controlled the reaction rate to give monodisperse spherical or disk-shaped QDs.

Article titled "From metal thiobenzoates to metal sulfide nanocrystals: An experimental and theoretical investigation" by Zhihua Zhang et al. published in *Nanomaterials*, 2012, 2, 113-133 reports a simple preparation of metal sulfide nanoparticles via the decomposition of thiobenzoate precursors at room temperature. Long chain alkyl amines were found to mediate the breakdown of metal thiobenzoates, such as those containing Ag, Cu, In and Cd, to produce uniform $Ag_2S$, $Cu_{2-x}S$, $In_2S_3$ and CdS nanoparticles respectively. For the synthesis of indium sulfide nanoparticles, InTB (0.3 mmol) was stirred in toluene (5 mL) at room temperature, and then 1.2 mmol of octylamine (OA) was injected to give a yellow solution. After storing for 6 hours, 10 mL of ethanol was added to induce the formation of turbidity. The particles were purified similarly to the previous procedure. For the preparation of oleylamine-capped In2S3 nanoparticles, it was found necessary to further add 40 µL of propylamine to speed up the reaction.

Article titled "The architecture of colloidal Quantum Dot solar cells: materials to devices" by Illan J. Kramer et al. published in Chemical Reviews, 2014, 114, 863-882 reports bulk-nano heterojunction CQD solar cells. The device architectures, and the enabling materials chemistry advances, that have enabled solar cells employing CQDs as the primary active layer to see rapid advances in solar power conversion efficiency.

Article titled "Synthesis and characterization of Poly (acrylic acid) stabilized Cadmium Sulfide Quantum Dots" by Serdar Celebi et al. published in *Journal of Physical Chemistry*, 2007, 111, 12668-12675 reports Cadmium sulfide (CdS) nanoparticles (NPs) capped with poly(acrylic acid) (PAA) were prepared in aqueous solutions from $Cd(NO_3)_2$ and $Na_2S$. Influence of the COOH/Cd ratio (0.8-12.5), reaction pH (5.5 and 7.5), and PAA molecular weight (2100 and 5100 g/mol) on the particle size, colloidal stability, and photoluminescence were investigated. In a typical synthesis, 64.3 mg of $Cd(NO_3)_2·4H_2O$ was dissolved in 100 mL of water and transferred into a 500 mL, three-necked round bottomed flask fitted with a mechanical stirrer. An appropriate amount of PAA (MW) 2100 g/mol) was dissolved in 150 mL of water, added to Cd solution, and deoxygenated with nitrogen for 10 min. For reactions run at pH 7.5, pH was adjusted with 10 M NaOH and/or 10 M $HNO_3$. Sulfide solution was prepared by dissolving 25 mg of $Na_2S·3H_2O$ in 50 mL of water and injected into the reaction mixture. The reaction mixture was kept stirring at room temperature under nitrogen for an hour. pH usually increases by 0.5-1.0 units after $Na_2S$ addition, and the reaction ends around pH 8.0-8.5. No further pH adjustment was done before UV-vis or PL measurements. An appropriate amount of PAA was calculated based on the desired COOH/Cd ratio.

Article titled "Colloidal PbS nanocrystals with size-tunable Near-Infrared Emission: Observation of post-synthesis self-narrowing of the particle size distribution" by M. A. Hines et al. published in *Advanced Materials*, 2003, 15(21), pp 1844-1849 reports the synthesis of nanocrystalline PbS quantum dots using organometallic precursors.

Article titled "Colloidally Prepared 3-Mercaptopropionic Acid Capped Lead Sulfide Quantum Dots" by Chase C. Reinhart et al. published in *Chemistry of Materials*, 2015, 27, 7313-7320 reports colloidally suspended PbS quantum dots stabilized with 3-mercaptopropionic acid (3-MPA) were prepared via solution ligand exchange. QDs were prepared by reacting lead acetate with a basic solution (pH=9) of 3-MPA before injecting a solution of $Na_2S$ and refluxing to grow QDs to different sizes.

Article titled "Lead Sulfide Quantum Dot Synthesis" published in Clean Energy Wiki, 2012 reports prepare reaction mixture with 14 gms of octadecene, 1.4 grams of oleic acid, 450 mg of lead oxide. When it mixes up it is murkly yellow at first and then becomes clear when it is heated up. Prepare the injection mixture from 4 gms of octadecene in 210 mL of hexylmethyldisilazane (HMDS). Once the reaction mixture has stabilized purge a syringe with nitrogen. Draw up the injection mixture and quickly insert it into the reaction vessel. Within second the mixture should turn a turbid black color. Let it react for 5 minutes and then quench the reaction in an ice bath. After it comes to room temperature transfer it to a separatory funnel.

Article titled "1.3 µm to 1.55 µm tunable electroluminescence from PbSe Quantum Dots embedded within an organic device" by J. S. Steckel et al. published in *Advanced Materials*, 2003, 15(21), pp 1862-1866 reports large area (mm² in size) infrared electroluminescent devices are demonstrated using colloidally grown PbSe quantum dots (QDs) in organic host materials. By changing the QD size the electroluminescence is tuned from λ=1.33-1.56 µm. The fabrication of this light-emitting device combines the thin film processing techniques available to organic materials with the tunable optical properties of PbSe QDs.

Article titled "Colloidal Quantum Dot Photovoltaics enhanced by Perovskite Shelling" by Zhenyu Yang et al. published in *Nano letters*, 2015, 15 (11), pp 7539-7543 reports photovoltaic devices based on inks of quantum dot on which grow thin perovskite shells in solid-state films. Passivation using the perovskite was achieved using a facile solution ligand exchange followed by postannealing. The resulting hybrid nanostructure created a more intrinsic CQD film, which, when incorporated into a photovoltaic device with graded bandstructure, achieved a record solar cell performance for single-step-deposited CQD films, exhibiting an AM1.5 solar power conversion efficiency of 8.95%.

Article titled "Photovoltaic performance of PbS Quantum Dots treated with metal salts" by Dong-Kyun Ko et al. published in *ACS Nano*, February 2016, 10 (3), pp 3382-3388 reports investigation on how the simultaneous introduction of metal cations and halide anions modifies the charge balance and enhances the solar cell efficiency. The addition of metal salts between QD deposition and ligand exchange with 1,3-BDT results in an increase in the short-circuit current and fill factor, accompanied by a distinct reduction in a crossover between light and dark current density-voltage characteristics.

The control on particle size of metal sulfide QDs is poor when using TMS in large scale synthesis by hot injection method. Further, there are no reports on large scale synthesis of PbS QDs by using TMS in hot injection methods. Large scale of PbS QDs had been synthesised by using TMS in non-injection diffusion controlled synthesis. But in this method really good size distribution of particles could not be realised, which clearly indicates broad absorption peak in the absorption spectra.

Therefore, there is a need for an alternative, cost-effective and at the same time safe and environmental friendly method for large scale metal sulfide QD production.

OBJECTIVES OF THE INVENTION

The main objective of the present invention is to provide a process for the preparation of metal sulphide QDs.

Another objective of the present invention is to provide a process for the preparation of colloidal QDs.

SUMMARY OF THE INVENTION

Accordingly, the present invention provides a process for the preparation of metal sulphide QDs comprising the steps of:
a) reacting a metal salt with a ligand in a solvent followed by heating at temperature ranging from 90 to 95° C. under vacuum for a period ranging from 1 to 2 h to afford a metal oleate or a metal amine solution;
b) preparing dithiocarbamic acid solution by mixing octyl dithiocarbamic acid with a ligand and a solvent followed by injecting to the metal oleate or metal amine solution of step (a) to obtain a solution;
c) injecting acetone to the solution of step (b) as an antisolvent to obtain a precipitate followed by collecting particles of precipitate by centrifugation to obtain metal sulfide QDs; and
d) dispersing said metal sulfide QDs in a non-polar solvent to obtain colloidal QDs.

In preferred embodiment, said metal is selected from the group consisting of Lead (Pb), Cadmium (Cd), Manganese (Mn), Zinc (Zn), Copper (Cu) and Tin (Sn).

In another preferred embodiment, said salt of the metal is selected from the group consisting of oxide salt, acetate salt and halide salts.

In still another preferred embodiment, said ligand is selected from oleic acid or oleyl amine.

In yet another preferred embodiment, said solvent of step (a) and (b) is 1-octadecene.

In still yet another preferred embodiment, said non-polar solvent of step (d) is selected from toluene, chloroform, hexane or octane.

In still yet another preferred embodiment, said particles of precipitate of step (c) are dispersed by adding a non polar solvent to obtain colloidal metal sulphide QDs.

In still yet another preferred embodiment, said metal sulfides QDs have particle size in the range of 2 nm to 10 nm.

In still yet another preferred embodiment, said metal sulphide QDs are used in optical devices selected from the group consisting of photovoltaic cells, photodetectors and light-emission devices.

Abbreviation:
QD: Quantum Dot
CQDs: Colloidal quantum dots
TMS: bis (tri methylsilyl) sulfide
DTCA: Octyl Dithiocarbamic Acid
HRMS: High Resolution Mass Spectrometry
NIR-UV: Near infra-red UV-Vis. Spectroscopy
HRTEM: High-resolution transmission electron microscopy
PXRD: Powder X-Ray Diffraction

DETAILED DESCRIPTION OF THE INVENTION

Figure 1A:
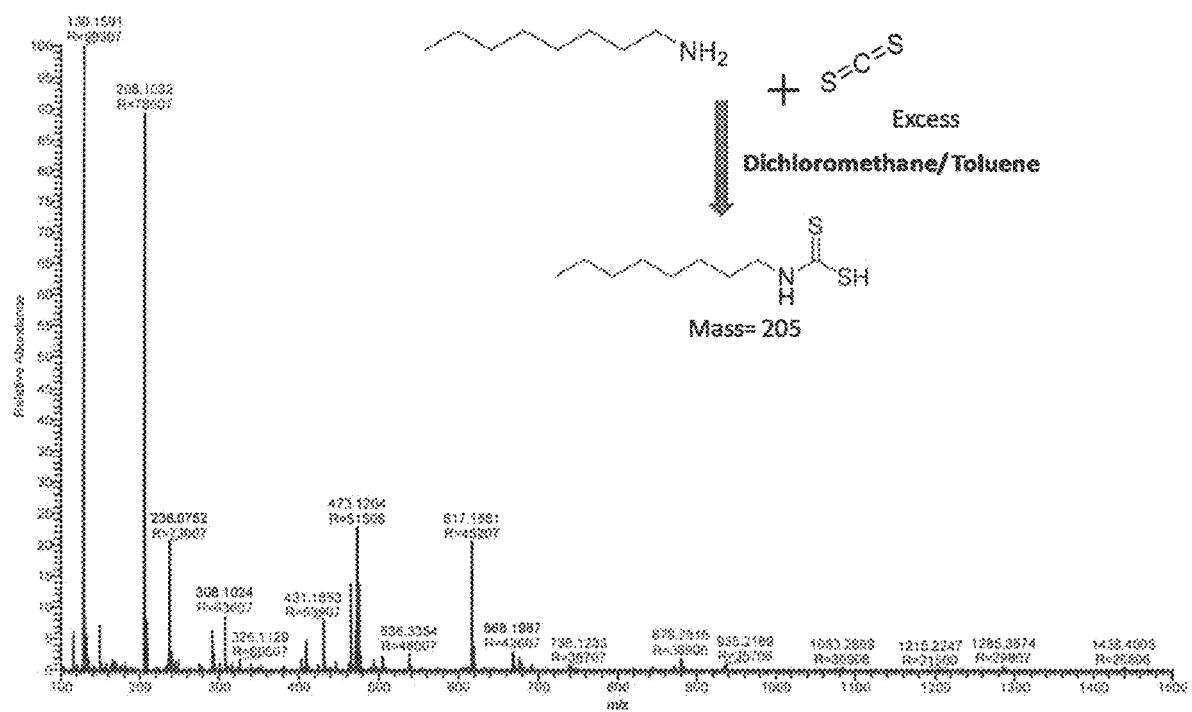
FIG. 1: Synthesis and characterisation of the Sulfur containing ligand DTCA (Octyl Dithiocarbamic Acid); (1a) HRMS data of DTCA indicates mass of the DTCA; (1b) NMR spectra of DTCA

The invention will now be described in detail in connection with certain preferred and optional embodiments, so that various aspects thereof may be more fully understood and appreciated.

The present invention provides a process for the preparation of metal sulphide quantum dots by using a very low cost sulphur precursor as a sulphur source.

In an embodiment, the present invention provides a process for the preparation of metal sulphide QDs comprising the steps of:
a) reacting a metal salt with a ligand in a solvent followed by heating at temperature ranging from 90 to 95° C. under vacuum for a period ranging from 1 to 2 h to afford a metal oleate or a metal amine solution;
b) preparing dithiocarbamic acid solution by mixing octyl dithiocarbamic acid with a ligand and a solvent followed by injecting to the metal oleate or metal amine solution of step (a) to obtain a solution;
c) injecting acetone to the solution of step (b) as an anti-solvent to obtain a precipitate followed by collecting particles of precipitate by centrifugation to obtain metal sulfide QDs; and
d) dispersing said metal sulfide QDs in a non-polar solvent to obtain colloidal quantum dots.

In preferred embodiment, said metal is selected from the group consisting of Lead (Pb), Cadmium (Cd), Manganese (Mn), Zinc (Zn), Copper (Cu) and Tin (Sn).

In another preferred embodiment, said salt of the metal is selected from the group consisting of oxide salt, acetate salt and halide salts.

In still another preferred embodiment, said ligand is selected from oleic acid or oleyl amine.

In yet another preferred embodiment, said solvent of step (a) and (b) is 1-octadecene.

In still yet another preferred embodiment, said non-polar solvent of step (d) is selected from toluene, chloroform, hexane or octane.

In yet still another preferred embodiment, said particles of precipitate of step (c) are dispersed by adding a non-polar solvent to obtain colloidal metal sulphide QDs.

In yet still another embodiment, said metal sulfides QDs have particle size in the range of 2 nm to 10 nm.

In yet still another embodiment, said metal sulfides QDs are stable and mono dispersed.

In yet still another embodiment, said metal sulfides QDs absorb and emit in visible to NIR region.

The present invention provides a process for the preparation of various metal sulphide QDs. More specifically the synthetic procedure involves two steps, wherein in the first step, Pb-oleate solution prepared by using Pb precursors [PbO, $PbCl_2$ or $Pb(ac)_2$] and oleic acid acting as a ligand dissolved in oleyl amine (in room temperature) and injected to the Pb-oleate solution at a particular temperature (80-140° C.) to obtain metal sulphide QDs with controlled particle size. From octyl dithiocarbamic acid, sulfur liberates as $H_2S$ in presence of amine at a particular temperature and as a side product thiourea also formed. The liberated $H_2S$ reacts with metal oleate and oleic acid capped metal sulfide QDs are formed.

The release rate of sulfur can be controlled by varying some reaction parameter like temperature and amine concentration. So, different sized QDs may be obtained by varying the release rate of sulfur. Octyl dithiocarbami acid based synthesis procedures have been used to produce tunable absorption spectra CQDs from 800-1300; with about 6 month air stability with narrow size distribution and comparable optical properties to the TMS based PbS QDS. The reaction scheme allowed in Scheme 1 as provided in FIG. 7.

The metal sulfide QDs of the present invention finds application in optical devices selected from the group consisting of photovoltaic cells, photodetectors and light-emission devices.

The colloidal metal sulfide QDs of the present invention finds application in optical devices selected from the group consisting of photovoltaic cells, photodetectors and light-emission devices.

The as prepared metal sulfide QDs readily go into and form clear dispersions with non-polar organic solvents such as toluene. This dispersion could be used in thin film photovoltaic solar cells.

Figure 2:
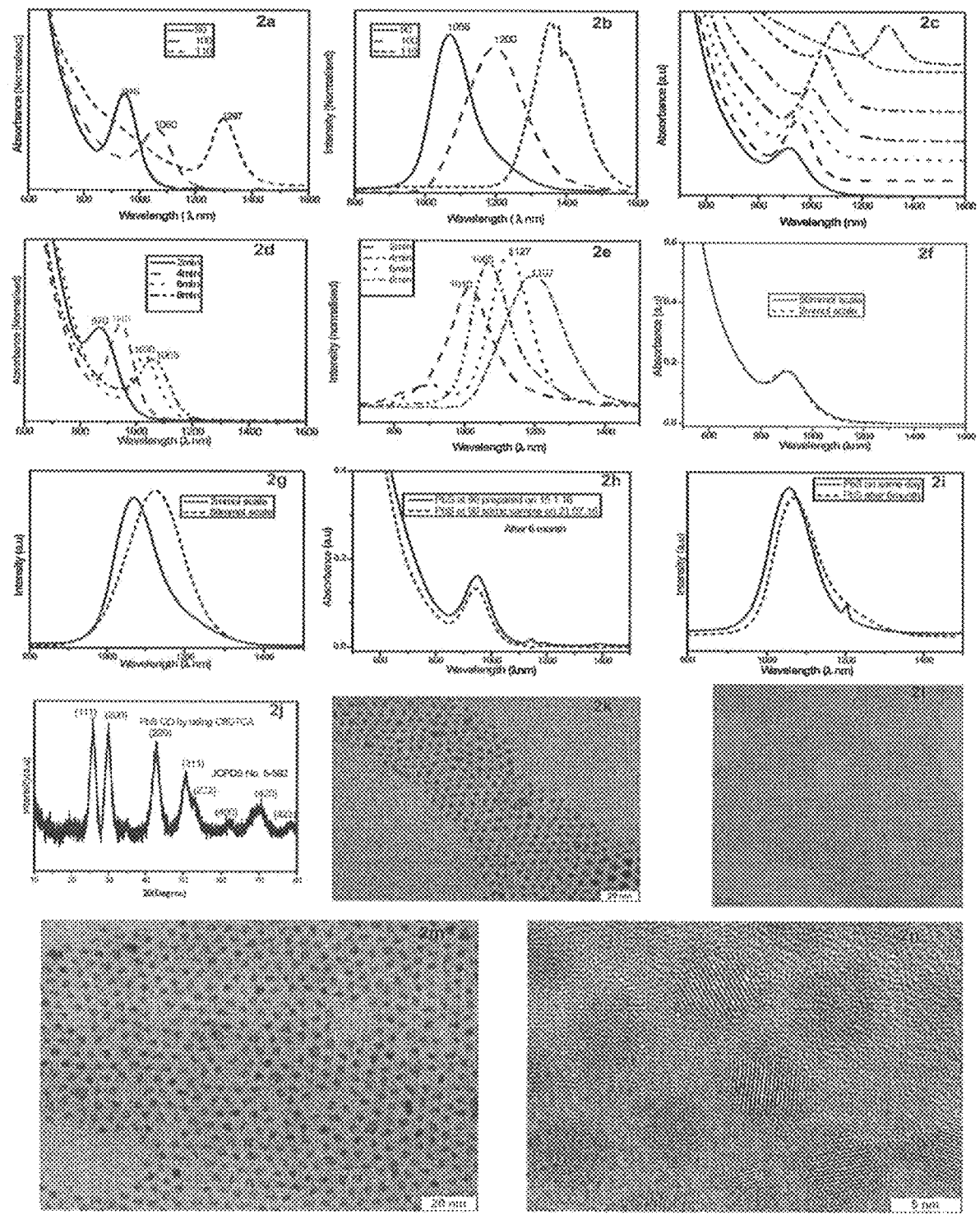
FIG. 2: Characterization of Lead sulfide QDS (PbS QDs); (2a) NIR-UV Spectra of oleic acid capped PbS QDs at different temperatures (90, 100 and 110° C.) (2b) NIR-Photo luminescence spectra of PbS QDs at different temperatures (90, 100 and 110° C.); (2c) Tunable NIR-UV spectra of PbS QDs prepared at different condition; (2d) NIR-UV Spectra of oleic acid capped PbS QDs at different time interval after injection of DTCA; (2e) NIR-Photo luminescence spectra of PbS QDs at different time; (2f, 2g) Scalability of PbS QDs from 2 mmol scale 50 mmol scale; (2f) NIR-UV Spectra of oleic acid capped PbS QDs; (2g) NIR-Photo luminescence spectra of PbS QDs; (2h, 2i) Stability of PbS QDs after 6 month; (2h) NIR-UV Spectra of oleic acid capped PbS QDs after 6 month; (2i) NIR-Photo luminescence spectra of PbS QDs after 6 month; (2j) PXRD of PbS QDs; (2k, 2l, 2m) TEM image of PbS QDs; (2n) HRTEM image of PbS QDS.

FIG. 1 depicts synthesis and characterization of the Sulfur containing ligand DTCA (Octyl Dithiocarbamic Acid); (1a) HRMS data of DTCA indicates mass of the DTCA; (1b) NMR spectra of DTCA FIG. 2 depicts characterization of Lead sulfide QDS (PbS QDs); (2a) NIR-UV Spectra of oleic acid capped PbS QDs at different temperatures (90, 100 and 110° C.), with temperature particle size increases and absorption peak shifts towards red; (2b) NIR-Photo luminescence spectra of PbS QDs at different temperatures (90, 100 and 110° C.), with temperature particle size increases and emission peak shifts towards red; (2c) Tunable NIR-UV spectra of PbS QDs prepared at different condition; (2d) NIR-UV Spectra of oleic acid capped PbS QDs at different time interval after injection of DTCA, with time particle size increases due to long growth time and absorption spectra clearly indicates red shift of excitonic peak; (2e) NIR-Photo luminescence spectra of PbS QDs at different time; (2f, 2g) Scalability of PbS QDs from 2 mmol scale 50 mmol scale; (2f) NIR-UV Spectra of oleic acid capped PbS QDs; (2g) NIR-Photo luminescence spectra of PbS QDs; (2h, 2i) Stability of PbS QDs after 6 month; (2h) NIR-UV Spectra of oleic acid capped PbS QDs after 6 month; (2i) NIR-Photo luminescence spectra of PbS QDs alter 6 month; (2j) PXRD of PbS QDs; (2k, 2l, 2m) TEM image of PbS QDs shows particles are highly monodispersed; (2n) HRTEM image of PbS QDS.

Figure 3:
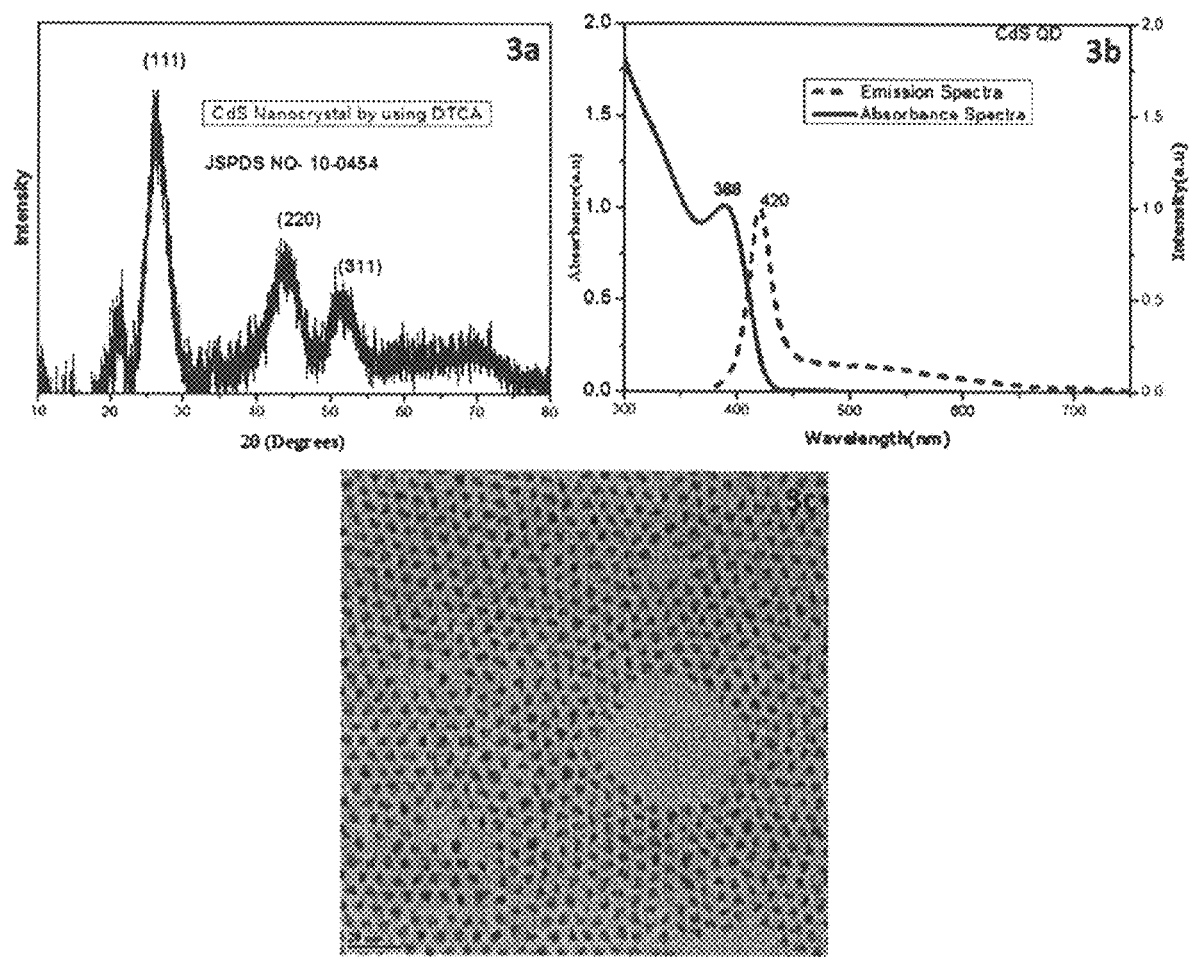
FIG. 3: Characterization of Cadmium sulfide QDS (CdS QDs) (3a) PXRD of CdS QDs; (3b) UV-Vis Spectra and Fluorescence spectra of CdS QDs; (3c) TEM image of CdS QDs.

FIG. 3 depicts characterization of Cadmium sulfide QDS (CdS QDs) (3a) PXRD of CdS QDs; (3b) UV-Vis Spectra and Fluorescence spectra of CdS QDs; (3c) TEM image of CdS QDs.

Figure 4:
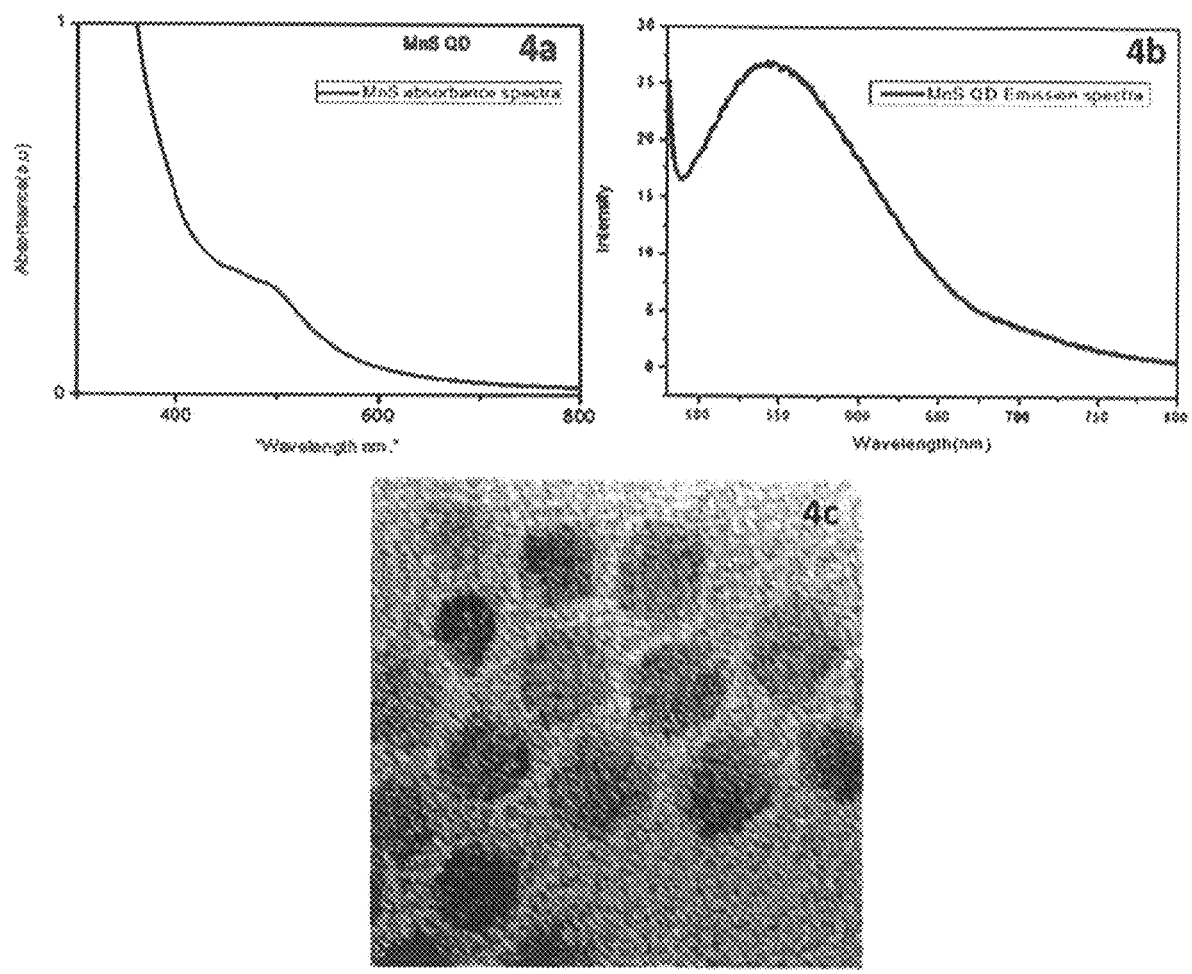
FIG. 4: Characterization of Manganese sulfide QDS (MnS QDs) (4a) UV-Vis Spectra of MnS QDs; (4b) Fluorescence spectra of MnS QDs; (4c) TEM image of MnS QDs.

FIG. 4 depicts characterization of Manganese sulfide QDS (MnS QDs) (4a) UV-Vis Spectra of MnS QDs; (4b) Fluorescence spectra of MnS QDs; (4c) TEM image of MnS QDs.

Figure 5:
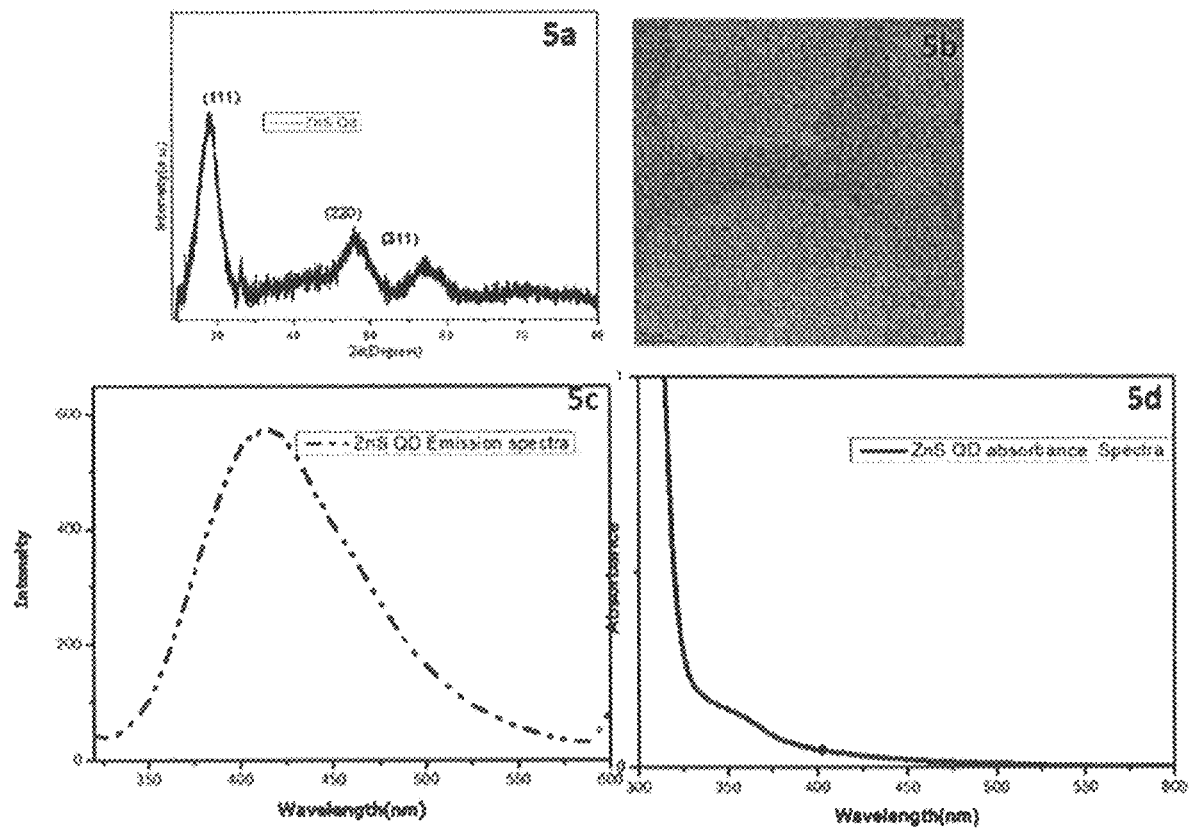
FIG. 5: Characterization of Zinc sulfide QDS (ZnS QDs) (5a) PXRD of ZnS QDs; (5b) TEM image of ZnS QDs; (5c) Fluorescence spectra of ZnS QDs; (5d) UV-Vis Spectra of ZnS QDS.

FIG. 5 depicts characterization of Zinc sulfide QDS (ZnS QDs) (5a) PXRD of ZnS QDs; (5b) TEM image of ZnS QDs; (5c) Fluorescence spectra of ZnS QDs; (5d) UV-Vis Spectra of ZnS QDS.

Figure 6:
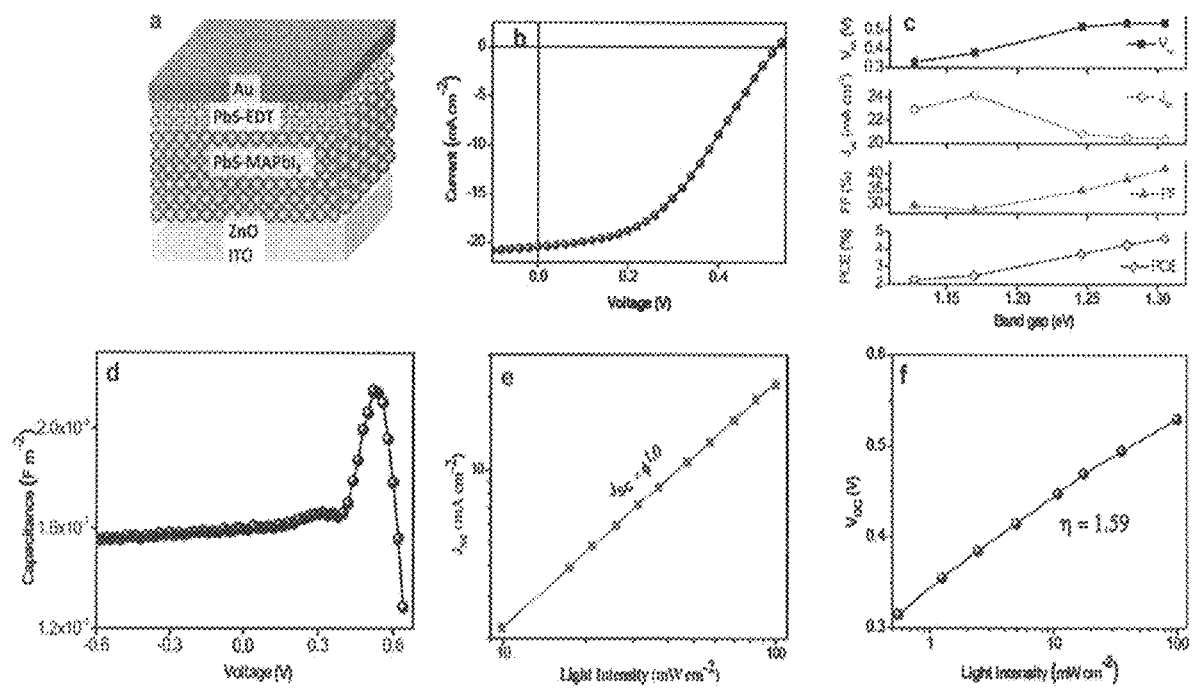
FIG. 6: (a) Schematic device structure of the photovoltaic device, (b) J-V characteristics of the best performing solar cell under 1.5 AM illumination, (c) Comparison of photovoltaic figure of merits for different band gap PbS QDs. (d) Capacitance-voltage plot for best performing PbS QD (1.3 eV band gap) based solar. (e) and (f) The evolution of short circuit current ($J_{sc}$) and open circuit voltage ($V_{oc}$) respectively for best performing PbS QD based solar cell

FIG. 6 depicts (a) Schematic device structure of the photovoltaic device, (b) J-V characteristics of the best performing solar cell under 1.5 AM illumination. (c) Comparison of photovoltaic figure of merits for different band gap PbS QDs. (d) Capacitance-voltage plot for best performing PbS QD (1.3 eV band gap) based solar. (e) and (f) The evolution of short circuit current ($J_{sc}$) and open circuit voltage ($V_{oc}$) respectively for best performing PbS QD based solar cell.

Figure 7:
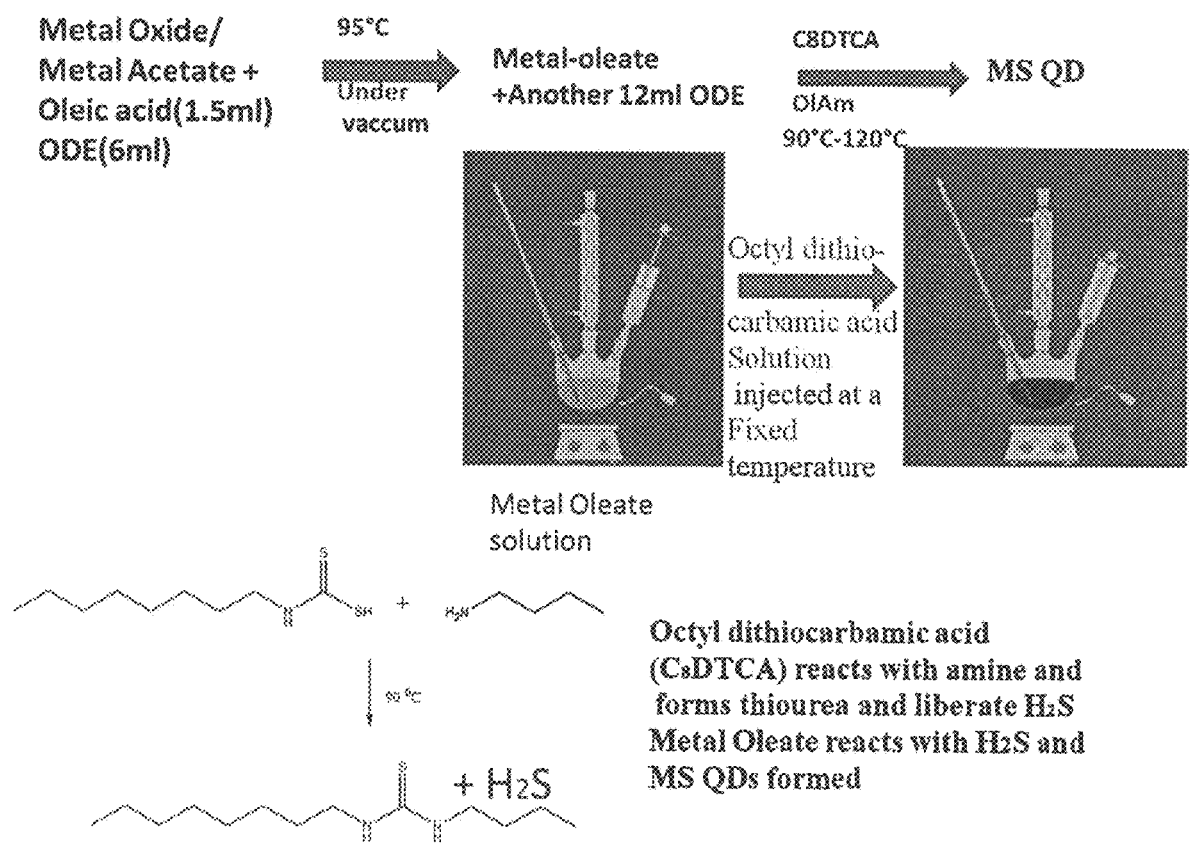
FIG. 7 shows scheme 1 which provides stepwise description of metal sulfide QDs synthesis using octyl dithiocarbamic acid

FIG. 7 shows scheme 1 which provides stepwise description of metal sulfide QDs synthesis using octyl dithiocarbamic acid.

EXAMPLES

Following examples are given by way of illustration therefore should not be construed to limit the scope of the invention.

Example 1: Synthesis of Octyl Dithiocarbamic Acid

About 50 ml toluene was taken in 250 ml Rb flask and cooled, and then 20 mmol of $CS_2$ (excess) added to it and stirred for some time. After 15 minute 10 mmol of Octyl amine added drop-wise into the $CS_2$ solution. After 30 min very shiny crystalline organic compound formed. It was washed by hexane and dried by vacuum and recrystallized. The obtained product was analyzed by NMR and HRMS. The NMR spectrum results White shiney crystal. $^1H$ NMR (200 MHz, Chloroform-d) δ 5.44 (s, 2H, N—H, S—H), 3.60-3.48 (m, 1H), 3.02 (t, J=7.3 Hz, 1H), 1.70-1.59 (m, 2H), 1.27 (m, 10H), 0.88 (t, J=6.1 Hz, 3H). HRMS Spectra of Octyl dithiocarbamic acid. Two major peak observed at ~130 and 206 due to Octyl Amine and Octyl dithiocarbamic acid respectively. In HRMS condition some of the compound (C8DTCA) decomposed to octyl amine.

Example 2: Synthesis of PbS QDS

A mixture of lead oxide (2 mmol, 0.45 g) or lead acetate (2 mmol), oleic acid (4 mmol, 1.26 ml) and 1-octadecene (8 mmol, 2.56 ml) in a flask was heated and degassed under vacuum at 95° C. for 1-2 h, followed by adding 15 ml of 1-octadecene. The temperature was set to 90-140° C. About 75 mg octyl dithiocarbamic acid (0.75 mmol) was dissolved in 0.5 ml oleyl amine and another 10 ml of 1-ODE added to it. The reaction was initiated by rapid injection of the dithiocarbamic acid solution. Immediately after injection, the heating mentle was removed and the flask was allowed to cool down gradually to room temperature under stirring. QDs were purified in air by adding acetone, followed by centrifugation. The extracted QDs were dispersed in toluene for solar cell fabrication. The purified PbS QDs were characterized by PXRD, UV-VIS spectroscopy, NIR-PL spectra and TEM. The PXRD pattern of the PbS nanocrystals prepared by this method is shown in FIG. 2j, which shows a high degree of crystallinity with all the peaks matching with the Bragg reflections of the standard cubic rock-salt structure of PbS (JCPDS #05-0592). The absorption and emission of these PbS nanocrystals could be tuned by varying the reaction parameter like temperature, time and octyldithiocarbamic acid concentration. It can be clearly seen that each of the sample displays well defined excitonic peak (absorption peak) and emission peak and the absorption peak position varied gradually from 915 to 1300 nm (1.35-0.95 eV) (FIG. 2c). The TEM image of this sample unveils the presence of monodispersed particles (particle sizes ranges 2.4-5 nm) which is also exemplified by their self assembly into two dimensional hexagonally close packed structures. High resolution TEM images showed in FIG. 2n indicates that the particles are highly crystalline with well-resolved lattice planes corresponding to an interplanar spacing of 0.29±0.02 nm, consistent with the (200) d-spacing of the PbS bulk rock salt structure.

Example 3: Synthesis of CdS QDs

Similarly a mixture of cadmium acetate (2 mmol) [not CdO, as it required very high temperatures about 300° C.], oleic acid (1 ml), oleyl amine (1 ml) and 1-octadecene (8 mmol, 2.56 ml) in a flask was healed and degassed under vacuum at 105° C. for 2-4 h, followed by adding 15 ml of 1-octadecene. The temperature was set to 160-200° C. About 75 mg octyl dithiocarbamic acid (0.75 mmol) was dissolved in 0.5 ml oleyl amine and another 10 ml of 1-ODE added to it. The reaction was initiated by rapid injection of the dithiocarbamic acid solution. Immediately after injection, the heating mentle was removed and the flask was allowed to cool down gradually to room temperature under stirring. QDs were purified in air by adding acetone and methanol, followed by centrifugation. The extracted QDs were dispersed in toluene. The purified CdS QDs were characterized by PXRD, UV-VIS spectroscopy, PL spectra and TEM. The PXRD patterns of these samples (FIG. 3a) confirm the formation of cubic phase (JCPDS-75-0581) of CdS. The UV-Vis and PL spectra (solid black line is the UV-Vis and dotted black line is photoluminescence spectra) of the CdS QDs prepared at 200° C. are displayed in FIG. 3b. The dotted black line (FIG. 3b) indicates pure band gap emission. High resolution TEM images showed in FIG. 3c indicate that the particles are highly crystalline and the average size calculated from TEM is ~3.3±0.5 nm.

Example 4: Synthesis of MnS QDs

Similarly a mixture of Manganese acetate (2 mmol), oleic acid (1 ml), oleyl amine (1 ml) and 1-octadecene (8 mmol, 2.56 ml) in a flask was heated and degassed under vacuum at 105° C. for 2-4 h, followed by adding 15 ml of 1-octadecene. The temperature was set to 160-200° C. About 75 mg octyl dithiocarbamic acid (0.75 mmol) was dissolved in 0.5 ml oleyl amine and another 10 ml of 1-ODE added to it. The reaction was initiated by rapid injection of the dithiocarbamic acid solution. Immediately after injection, the heating mentle was removed and the flask was allowed to cool down gradually to room temperature under stirring. QDs were purified in air by adding acetone and methanol, followed by centrifugation. The extracted QDs were dispersed in toluene. The purified MnS QDs were characterized by PXRD, UV-VIS spectroscopy, PL spectra and TEM. The UV-Vis and PL spectra (FIG. 4a is the UV-Vis and FIG. 4b is photoluminescence spectra) of the MnS QDs prepared at 200° C. are displayed in FIG. 4. The dotted black line (FIG. 4b) indicates pure band gap emission. High resolution TEM images showed in FIG. 4c indicate that the particles are highly crystalline and the average size calculated from TEM is ~6.9±1.6 nm.

Example 5: Synthesis of ZnS QDs

Similarly a mixture of Zinc acetate (2 mmol), oleic acid (1 ml), oleyl amine (1 ml) and 1-octadecene (8 mmol, 2.56 ml) in a flask was heated and degassed under vacuum at 105° C. for 2-4 h, followed by adding 15 ml of 1-octadecene. The temperature was set to 160-200° C. About 75 mg octyl dithiocarbamic acid (0.75 mmol) was dissolved in 0.5 ml oleyl amine and another 10 ml of 1-ODE added to it. The reaction was initiated by rapid injection of the dithiocarbamic acid solution. Immediately after injection, the healing mentle was removed and the flask was allowed to cool down gradually to room temperature under stirring. QDs were purified in air by adding acetone, followed by centrifugation. The extracted QDs were dispersed in toluene. The purified ZnS QDs were characterized by PXRD, UV-VIS spectroscopy, PL spectra and TEM. The PXRD patterns of these samples (FIG. 5a) confirm the formation of cubic phase (JCPDS-05-566) of ZnS. The UV-Vis and PL spectra (FIG. 5d is the UV-Vis and FIG. 5c is photoluminescence spectra) of the ZnS QDs prepared al 200° C. are displayed in FIG. 5. The dotted black line (FIG. 5c) indicates pure band gap emission. High resolution TEM images showed in FIG. 5b indicate that the particles are highly crystalline and the average size calculated from TEM is ~3.5±0.5 nm.

Example 6: Perovskite Ligand Exchange and Film Fabrication

The oleic acid capped PbS CQDs were synthesized by using $C_8DTCA$ as a sulphur source. The perovskite solution-phase ligand exchange was carried out in Argon atmosphere. The perovskite ligand exchange was carried out and purified by slightly modified to previously reported method. The starting concentration of CQD solution was set at ~10 mg/ml in octane. For solution-phase ligand exchange, 5 mL of dimethyl formamide (DMF) solvent containing 0.1 M of $PbI_2$ and 0.02 M of $PbBr_2$ and 0.1 M of MAI were added to the vial and mixed vigorously at 45-50° C. for about 20-30 minutes. A 5 ml of PbS CQD octane solution (10 mgml$^{-1}$) was added to 5 ml of precursor solution in Argon atmosphere. These were mixed vigorously for 1-2 min until the CQDs completely transferred to the DMF phase. The DMF solution was washed three times with octane to remove the residual OA ligands. After ligand exchange, CQDs were precipitated via die addition of toluene, and were separated by centrifugation. After 20 min of drying, the CQDs were then redispersed in butylamine (200 mgml$^{-1}$) to facilitate the film deposition. The exchanged ink was deposited by single-step spin-coating at 2,500 r.p.m. for 30 s to achieve~200 nm thickness.

Example 7: PbS CQDs Solar Cell Fabrication

The solar cells were prepared on a pre-patterned ITO substrate (2.5 cm×2.5 cm). Two layers of ZnO nanoparticles were deposited on the substrate by spin coating at 3500 rpm. The perovskite-capped CQD film was further annealed at 70° C. for 10 min under nitrogen, atmosphere. Two layers of EDT ligand exchanged CQDs were deposited on top of perovskite-capped CQD film by spin-casting following reported method. Top electrodes were deposited by thermal evaporator from Hind high vacuum, model BC-300 at a base pressure of $3\times10^{-6}$ mBar. 10 nm MoO$_3$ was deposited at 0.1 Ås$^{-1}$, followed by 50 nm of Au deposition at 0.5 Ås$^{-1}$ and finally 100 nm Ag was deposited at 1 Ås$^{-1}$ to complete the film formation.

Advantages of the Invention

1. The present invention gives access to large quantities of monodispersed metal sulfide QDs with good optical properties.
2. The as prepared metal sulfide QDs readily go into and form clear dispersions with non-polar organic solvents such as toluene. This dispersion could be used in thin film photovoltaic solar cells.
3. The key advantage that process can be done in continuous flow method for industrial scale synthesis.
4. The synthesized PbS QDs are air-stable for several months (more than 3 months) and they readily self-assemble into ordered lattices and present simple low-cost method resulted in a record solar power conversion efficiency of 4.64%.

We claim:

1. A process for the preparation of metal sulphide QDs comprising the steps of:
    a) reacting a metal salt with a ligand in a solvent followed by heating at a temperature ranging from 90 to 95° C. under a vacuum for a period ranging from 1 to 2 h to afford a metal oleate or a metal amine solution;
    b) preparing a dithiocarbamic acid solution by mixing octyl dithiocarbamic acid with a ligand and a solvent to form a mixture followed by injecting said mixture to the metal oleate or metal amine solution of step (a) to obtain a dithiocarbamic solution;
    c) injecting acetone to the dithiocarbamic solution of step (b) as an anti-solvent to obtain a precipitate, followed by collecting particles of precipitate by centrifugation to obtain metal sulfide QDs; and
    d) dispersing said metal sulfide QDs in a non-polar solvent to obtain colloidal quantum dots.

2. The process as claimed in claim 1, wherein said metal is selected from the group consisting of Lead (Pb), Cadmium (Cd), Manganese (Mn), Zinc (Zn), Copper (Cu) and Tin (Sn).

3. The process as claimed in claim 1, wherein said salt of the metal is selected from the group consisting of an oxide salt, an acetate salt and a halide salt.

4. The process as claimed in claim 1, wherein said ligand is selected from the group consisting of oleic acid and oleyl amine.

5. The process as claimed in claim 1, wherein said solvent of step (a) and (b) is 1-octadecene.

6. The process as claimed in claim 1, wherein said non-polar solvent of step (d) is selected from the group consisting of toluene, chloroform, hexane or octane.

7. The process as claimed in claim 1, wherein said metal sulfide QDs have a particle size in the range of 2 nm to 10 nm.

8. The process as claimed in claim 1, wherein said metal sulfides QDs are stable and mono dispersed.

9. The process as claimed in claim 1, wherein said metal sulfides QDs absorb and emit in visible to NIR region.

* * * * *